(12) United States Patent
Snyder et al.

(10) Patent No.: US 7,303,537 B1
(45) Date of Patent: Dec. 4, 2007

(54) AMBULATION ASSISTANCE DEVICE

(76) Inventors: Jean M. Snyder, 2019 330th Ave., Sidney, IA (US) 51652; Roger L. Snyder, 2019 330th Ave., Sidney, IA (US) 51652

( * ) Notice: Subject to any disclaimer, the term of this patent is extended or adjusted under 35 U.S.C. 154(b) by 293 days.

(21) Appl. No.: 11/117,119

(22) Filed: Apr. 28, 2005

(51) Int. Cl.
*A61F 5/00* (2006.01)

(52) U.S. Cl. .............................. 602/16; 602/27; 135/68; 135/74

(58) Field of Classification Search ................ 602/5, 602/16, 26, 27; 135/65, 68, 69, 71, 74–75
See application file for complete search history.

(56) References Cited

U.S. PATENT DOCUMENTS

| | | | | |
|---|---|---|---|---|
| 3,633,967 A | * | 1/1972 | Timmins | 297/423.45 |
| 5,300,016 A | * | 4/1994 | Marlatt | 602/16 |
| 5,941,263 A | * | 8/1999 | Bierman | 135/68 |
| D419,288 S | * | 1/2000 | Hartfield | D3/7 |
| 6,494,919 B1 | * | 12/2002 | Matthews | 623/32 |
| 6,799,592 B1 | * | 10/2004 | Reynolds | 135/74 |

* cited by examiner

*Primary Examiner*—Michael A. Brown
(74) *Attorney, Agent, or Firm*—Dennis L. Thomte; Thomte Law Office

(57) ABSTRACT

An ambulation assistance device is provided with a leg support that releasably secures to an individual's leg and supports the leg in a positively flexed position. An elongated pylon extends downwardly from the leg support and may be hinged at the point of connection to simulate the mechanics of the individual's knee during ambulation. A resilient rearward brace may be used to bias the pylon toward a standing position. A forward brace may be provided to limit over extension of the pylon. A foot member may be pivotably coupled with the distal end of the pylon to simulate the mechanics of the individual's ankle during ambulation. A resilient brace may bias the foot member toward a standing position.

17 Claims, 3 Drawing Sheets

AMBULATION ASSISTANCE DEVICE

BACKGROUND OF THE INVENTION

1. Field of the Invention

The present invention relates to ambulation assistance devices and more particularly to a device that may be releasably coupled to an individual's leg in a flexed position, such that the individual is able to stand and walk with some regularity without placing significant weight or pressure on the individual's foot or ankle. Just as important however, the device frees the individual's arms and hands for balance and engaging in various activities.

2. Description of the Prior Art

Lower leg injuries, such as torn tendons or broken bones to the foot or ankle are commonplace. Such injuries typically require that the individual permit the injured leg to heal over a lengthy period of weeks or months without placing any significant weight or pressure onto the affected areas of the leg. Accordingly, the injured individual is forced to go about their daily activities using crutches or a wheelchair. However, anyone who has spent any amount of time in a wheelchair knows that most surrounding environments are less than wheelchair friendly, oftentimes making the wheelchair more of a burden than a helpful tool for getting from one place to another.

Crutches are easier than wheelchairs at times due to the fact that they may be easily stored when the individual must drive an automobile or sit in an area that is not accessible by wheelchair. Crutches also make it possible, even if very difficult, to navigate stairways, grassy slopes, and other such areas that are not as easily navigated with a wheelchair. However, crutches occupy the use of both arms and hands, preventing an individual from easily caring items from one location to another. An individual must also keep the lower portion of the leg in an elevated position, in front or behind the individual, while walking from one place to another. This can become quite difficult over long distances, especially when the individual is wearing a cast or brace on the affected area.

Clearly one of the greatest drawbacks to the use of wheelchairs or crutches is that the individual is unable to ambulate in a generally natural fashion. Accordingly, the individual is unable to easily complete routine tasks or move long distances under their own power. More than an inconvenience, the fact that prior art devices fail to mimic natural support and movement creates a risk of injury when the individual attempts to climb or descend a flight of stairs, for example. Moreover, the prior art devices and methods of ambulation, while successful in keeping weight forces from the affected area of the leg, also limit the natural movement and exercise of the upper portions of the individual's leg. Prolonged periods of using such prior art devices can cause various levels of muscle atrophy and a degradation of the individual's dexterity.

Accordingly, what is needed is an ambulation assistance device that permits an individual to move under their own power from one location to another, without placing a significant amount of weight or pressure on the lower portion of the individual's leg, and enables a user to retain free use of the individual's arms and hands. Moreover, such a device should closely mimic the individual's natural movement in order to promote safety and provide a limited amount of exercise to the unaffected portions of the individual's leg.

SUMMARY OF THE INVENTION

The ambulation assistance device of the present invention is generally provided with a leg support that is shaped to releasably engage a forward portion of an individual's knee and at least a forward portion of the individual's lower leg in a positively flexed position. An elongated pylon is coupled with, and extends downwardly from, the leg support. A foot member is positioned adjacent a distal end portion of the pylon for releasably engaging an operating surface and providing positive traction between the pylon and the operating surface. In one embodiment, straps may be placed around the individual's leg to secure the leg to the leg support. The pylon may be pivotably coupled with the leg support so that the pylon may be selectively pivoted into a rearwardly flexed position while the individual walks. A resilient rear brace member may be provided to extend from the leg support to an approximate mid point on the pylon so that the pylon is biased toward a generally perpendicular, or standing, position with respect to the leg support. A generally rigid forward brace member may be provided to extend upwardly and forwardly from the pylon, in one preferred embodiment, and releasably engage a forward portion of the leg support in order to limit movement of the pylon from a standing position to a forward flexion position.

The foot member may be provided in a generally elongated shape and pivotably coupled at a point approximating its midpoint to the distal end portion of the pylon so that the pylon may be selectively moved between a standing position and a forward positive flexion position with respect to the foot member. A resilient brace member may be coupled with the foot member and the pylon such that the pylon is biased toward a standing position with respect to the foot member. A bracket is provided in one embodiment to prevent the pylon from moving into a rearward positive flexion position with respect to the foot member.

In another preferred embodiment, the pylon is length adjustable to accommodate individuals of various heights. The leg support may also be hinged in order to allow the individual to straighten the leg, without removing the device.

Therefore, a principle object of the present invention is to provide an ambulation assistance device that generally mimics natural leg mechanics and permits an individual to move from one location to another without the use of the individual's upper extremities.

A further object of the present invention is to provide an ambulation assistance device that is releasably secured to an individual's leg and supports the lower portion of the leg in a positively flexed position.

Still another object of the present invention is to provide an ambulation assistance device that is releasably secured to an individual's leg in a manner that permits the individual to move from one location to another without placing significant weight or pressure on the individual's foot or ankle.

A further object of the present invention is to provide an ambulation assistance device that supports an individual's leg in a positively flexed position and provides a support structure having a pair of hinges that simulate the individual's knee and ankle joints during ambulation.

Still another object of the present invention is to provide an ambulation assistance device that relieves a lower end portion of an individual's leg from bearing weight or pressure while permitting the upper portion of the leg to exercise and function in a relatively normal fashion.

Yet another object of the present invention is to provide an ambulation assistance device that is relatively simple in construction and use.

These and other objects of the present invention will be apparent to those having skill in the art.

DESCRIPTION OF THE PREFERRED EMBODIMENT

In the following detailed description of exemplary embodiments, reference is made to accompanying FIGS. 1-4, which form a part hereof and show, by way of illustration, exemplary embodiments of the present invention. These embodiments are disclosed in sufficient detail to enable those skilled in the art to practice the invention. It is to be understood that other embodiments may be utilized, however, and other changes may be made without departing from the spirit or scope of the present invention. The following detailed description is, therefore, not to be taken in a limiting sense in that the scope of the present invention is defined only by the appended claims.

Figure 1:
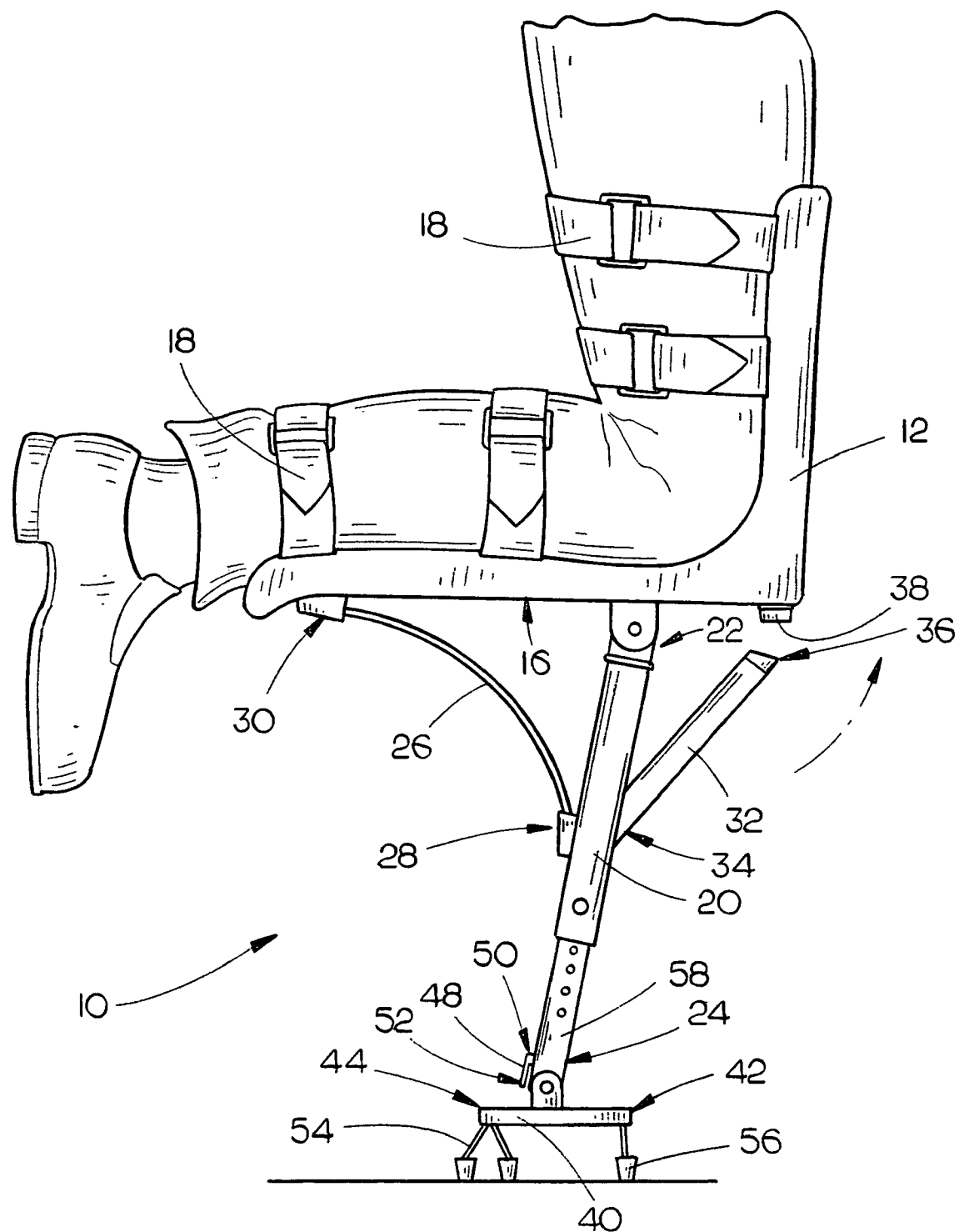
FIG. 1 depicts a side elevation view of one preferred embodiment of the ambulation assistance device of the present invention as the same could be worn and used by an individual for forward ambulation.
Figure 2:
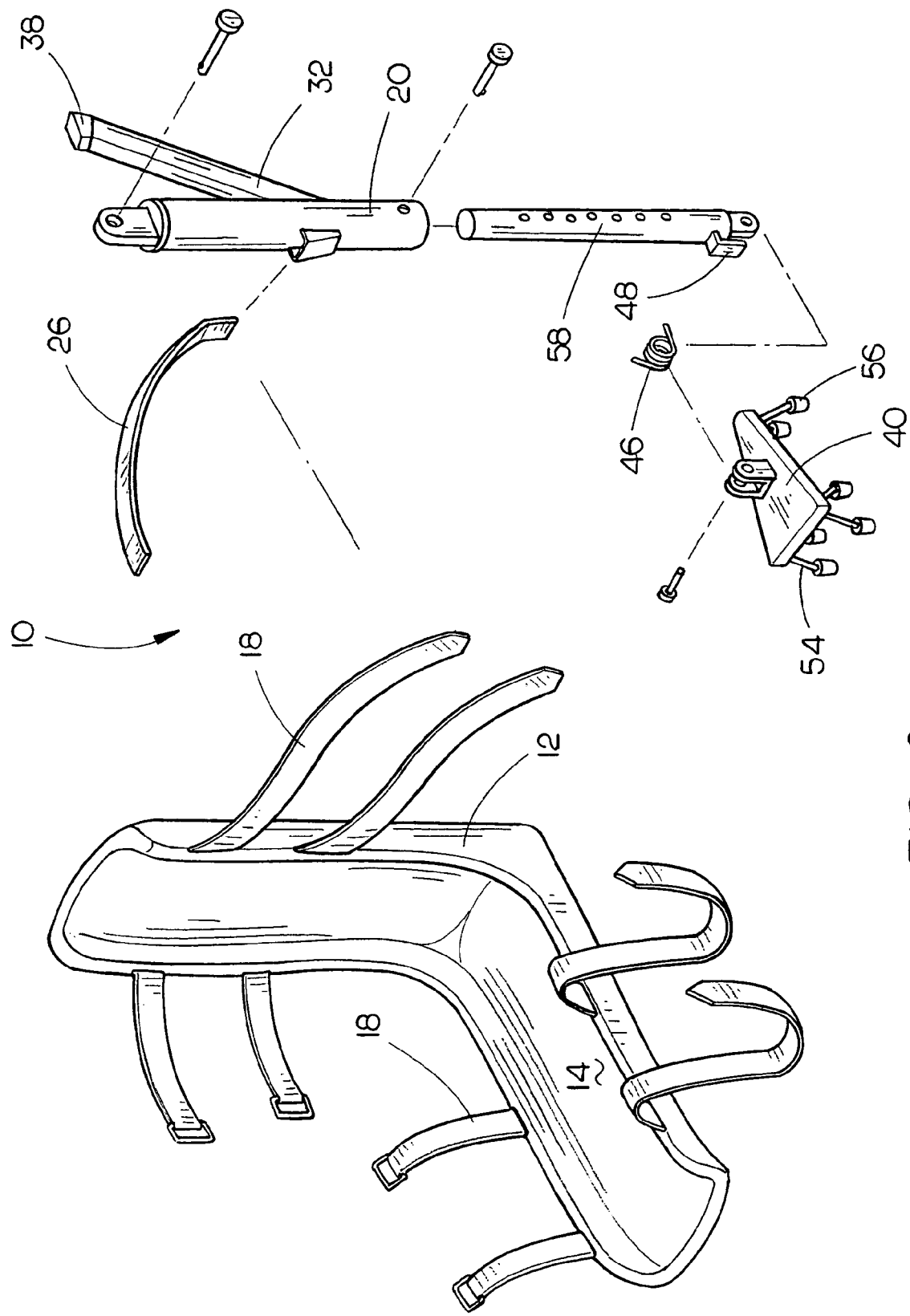
FIG. 2 is a partially exploded view of the ambulation assistance device depicted in FIG. 1.
Figure 4:
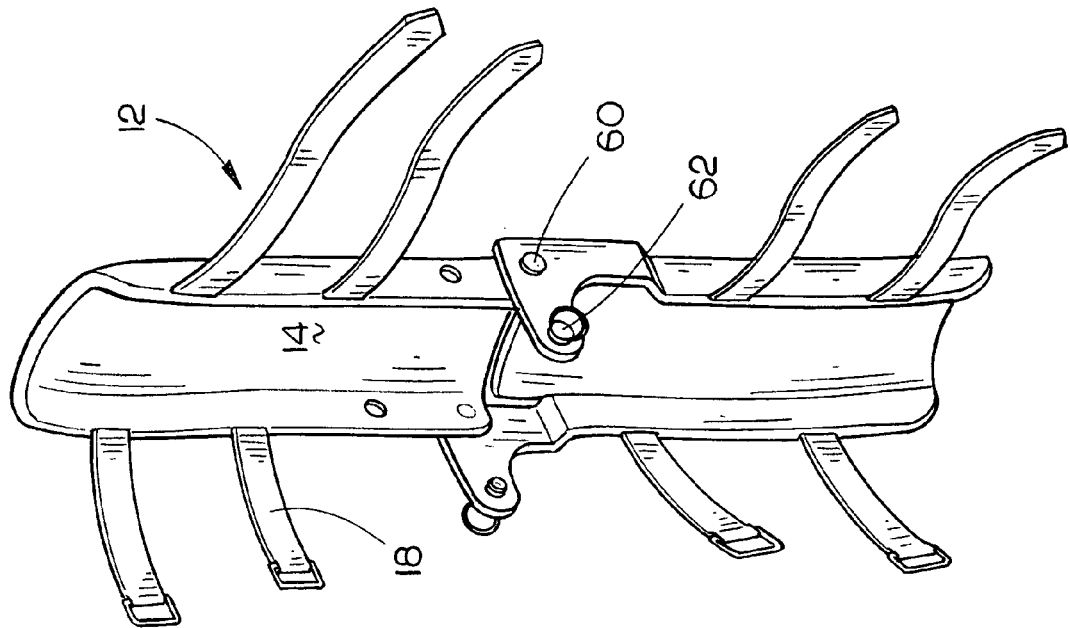
FIG. 4 is an isometric view of the leg support depicted in FIG. 3 in a fully extended position.
Figure 3:
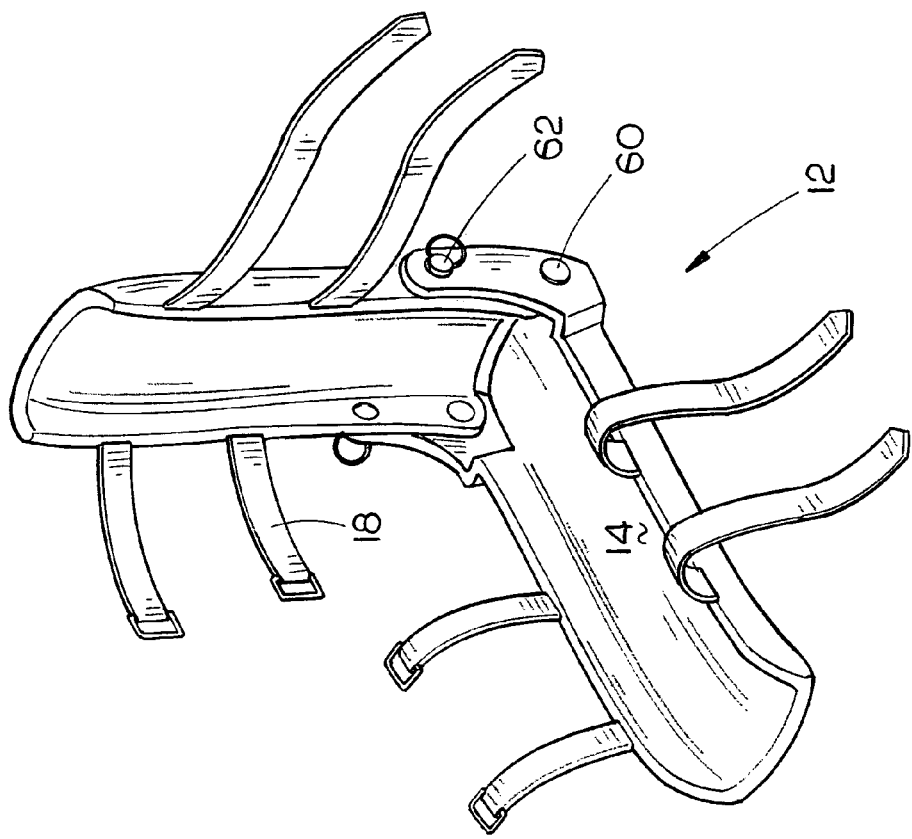
FIG. 3 is an isometric view of an alternate embodiment of the leg support portion of the ambulation assistance device of the present invention.

The ambulation assistance device 10 of the present invention is provided with a leg support 12, having an upper surface 14 and a lower surface 16. The upper surface 14 is shaped to releasably engage a forward portion of an individual's knee and at least a forward portion of the individual's lower leg, when the individual's leg is positively flexed, as depicted in FIG. 1. It is contemplated that the upper surface 14 of the leg support 12 may be flat. However, comfort and performance will generally dictate a slightly curved, elongated channel that will generally conform to the individual's leg. It is contemplated that side portions may be provided to the leg support 12 that extend upwardly along the sides of the individual's leg. Such side portions could be configured to provide a friction-fit engagement with the individual's leg, comfortably securing the device 10 thereto. However, other methods of securing the device 10 to the individual's leg are contemplated, such as a plurality of straps 18 that may be positioned along the leg support to at least partially wrap around the upper and lower portions of the individual's leg in a secure but comfortable fashion. One or more types of padding, such as a closed-cell foam could be provided to both the upper surface 14 of the leg support 12 and the straps 18 in order to provide additional comfort to the individual.

A generally elongated pylon 20, having an upper end portion 22 and a lower end portion 24, is coupled with and extends downwardly from the leg support 12. It is contemplated that, in certain situations, that the upper end portion 22 of the pylon 20 could be rigidly secured with the leg support 12, in order to promote stability. However, in a preferred embodiment, the upper end portion 22 of the pylon 20 is pivotably engaged with the leg support 12. This manner of engagement permits the pylon 20 to be selectively moveable between a standing position, which is generally perpendicular in relationship to the leg support 12, and a flexion position, which positions the pylon 20 in an acute angular relationship to a forward portion of the leg support 12. Accordingly, the pivoting connection between the leg support 12 and the pylon 20 may simulate the general mechanics of the individual's knee during normal ambulation.

Where the pylon 20 is placed in a pivotable engagement with the leg support 12, a resilient rear brace member 26 may be coupled at a first end portion 28 to a point on the pylon 20 that is between the upper end portion 22 and the lower end portion 24, and at a second end portion 30 to a rearward portion of the leg support 12. A deformably resilient structure, such as the plate spring, which is depicted in FIG. 1, will be preferred so that the pylon 20 is biased toward a standing position. Accordingly, as an individual moves the device 10 in a forward direction, the pylon 20 will move to a rearward flexed position. When the individual lifts the device 10 from the operating surface, the rear brace member 26 will return the pylon 20 to a standing position. The geometric positioning of the rear brace member 26 along the leg support 12 and the pylon 20, as well as the material as chosen, may be dictated according to the desired level of structural bracing provided to the device 10 by the rear brace member 26.

In a preferred embodiment, where the pylon 20 is pivotably coupled with the leg support 12, a forward brace member 32, having a first end portion 34 and a second end portion 36, may be secured between a forward portion of the leg support 12 and the pylon 20. In one preferred arrangement, the first end portion 34 is secured to the pylon 20 at a point between the upper end portion 22 and the lower end portion 24. The forward brace member 32 extends upwardly, wherein the second end portion 36 is left free from structural attachment to the leg support 12. However, the second end portion 36 of the forward brace member 32 is positioned to engage the leg support 12 and limit the travel of the pylon 20 to a position of forward flexion with respect to the leg support 12. One or more bumpers 38 may be positioned adjacent the second end portion 36 and/or along the leg support 12 to cushion an engagement force between the second end portion 36 and the leg support 12. Various deformably resilient materials would suffice for the construction of the bumpers 38.

The lower end portion 24 of the pylon 20 should be provided with a foot means for releasably engaging the operating surface and providing positive traction between the pylon 20 and the operating surface. Accordingly, the pylon 20 may be left in an elongated peg design and be provided with a generally resilient bumper or covering adjacent the lower end portion 24. Various resilient materials, such as rubber, would provide a desirable cushion and degree of positive traction with most operating surfaces. However, in a preferred embodiment, the foot means is comprised of a base 40, having a forward end portion 42 and a rearward end portion 44. It is contemplated that the base 40 may be provided in nearly any shape and size, according to the level of stability and contact surface desired between the base 40 and the operating surface. It is contemplated that certain situations may dictate that the lower end portion 24 of the pylon 20 be rigidly engaged with the base 40. However, a preferred embodiment provides a pivoting connection between the pylon 20 and the base 40 so that the pylon 20 may be selectively moved between a standing position, which is generally perpendicular to the base 40, and a forward, positively flexed position with respect to the base 40. This structural orientation will simulate the mechanical operation of the individual's ankle during normal ambulation. A resilient brace member 46 may be coupled with the pylon 20 and the base 40 in such a manner that the pylon 20 is biased toward the standing position with respect to the base 40. Deformably resilient structures, such as plate and coiled springs may be desirable for constructing the brace member 46. However, other similar structures are contemplated. A bracket 48 may be secured adjacent the pylon 20 and the base 40 in a manner that limits movement of the pylon 20 from a standing position to a position of rearward positive flexion, with respect to the base 20. One such embodiment, depicted in FIG. 1 provides a bracket 48 having a first end portion 50 secured to the pylon 20 and a second free end portion 52 that is positioned to engage the base 40 at a desired angular orientation between the pylon 20 and the base 40.

The base 40 may be provided with one or more protrusions 54 that extend between the base 40 and the operating surface. The protrusions 54 may be provided in a variety of structural configurations and position with respect to one another according to the desired use of the device 10. The protrusions 54 may be provided with various tips 56 that may be shaped in a cleat fashion to engage soft ground surfaces while being formed of a material that will engage hardened operating surfaces to provide a desirable level of traction. Other structures such as pads, curved bumpers, casters, wheels, and the like may also be coupled with the base 40 in various arrangements.

In certain settings, such as general hospital use, the device 10 should be provided in an adjustable fashion so that it may be used at different times by various individuals of different dimensions. For example, the pylon 20 may be length adjustable, by providing an extension 58 that may be slidably secured to the pylon 20 in one of several adjustment stops to provide a desired length for a particular user Likewise, the leg support 12 could be releasably engageable with the pylon 20, such that one of various different sizes of leg supports 12 could be used to accommodate an individual having unique proportions.

In order to provide a degree of flexibility to the device 10 and enable the individual to sit comfortably or simply straighten his or her leg, the leg support 12 may be provided with a hinge 60 closely adjacent a point where the upper surface 14 of the leg support 12 would engage the individual's knee. One or more locking pins 62 or other mechanical locking device may be provided for securing the leg support 12 in a flexed position. To the extent that an individual moves to a seated position while wearing the device 10, it is contemplated that the individual may want the pylon 20 and base 42 to rest on the operating surface and not project outwardly from the individual's leg. Accordingly, the rear brace member 26 should be coupled with the leg support 12 and pylon 20 in a manner that permits its easy removal. In the example depicted in FIG. 1, the plate spring is easily removed from the opposing receiving blocks, which permits the pylon 20 to pivot downwardly until the lower end portion 24 rests closely adjacent the operating surface.

In the drawings and in the specification, there have been set forth preferred embodiments of the invention and although specific items are employed, these are used in a generic and descriptive sense only and not for purposes of limitation. Changes in the form and proportion of parts, as well as a substitution of equivalents, are contemplated as circumstances may suggest or render expedient without departing from the spirit or scope of the invention as further defined in the following claims.

Thus it can be seen that the invention accomplishes at least all of its stated objectives.

We claim:

1. An ambulation assistance device for use with an individual's leg, the device comprising:
    a leg support, having upper and lower surfaces; said upper surface being shaped to releasably engage a forward portion of the individual's knee and at least a forward portion of a lower portion of the individual's leg when the lower portion of the individual's leg is positively flexed;
    a generally elongated pylon operatively coupled with and extending downwardly from said leg support; said pylon being pivotably coupled with said leg support in a manner that permits said pylon to be selectively moved between a standing position, which is generally perpendicular in relationship to said leg support, to a flexion position, which positions said pylon in an acute angular relationship to a rearward portion of said leg support;
    foot means adjacent a distal end portion of said pylon for releasably engaging an operating surface and providing positive traction between said pylon and said operating surface; and
    a resilient rear brace member operatively coupled at one end portion to the rearward portion of said leg support and at an opposite end portion to a point on said pylon that is between opposite end portions of said pylon so that said pylon is biased toward said standing position.

2. The device of claim 1 wherein said leg support is angularly shaped to releasably engage a forward portion of an upper portion of the individual's leg and support the individual's leg in a position approximating ninety degrees flexion at the knee.

3. The device of claim 2 wherein said leg support is hinged, adjacent a point where said leg support is shaped to engage the individual's leg, such that the individual may selectively straighten said leg support and the individual's leg simultaneously.

4. The device of claim 3 further comprising a plurality of straps that are positioned on said leg support to at least partially wrap around the upper and lower portions of the individual's leg to secure the individual's leg adjacent said leg support.

5. The device of claim 1 wherein said rear brace member is comprised of a spring.

6. The device of claim 1 further comprising a forward brace member that operatively engages said pylon and said leg support in a manner that limits movement of said pylon from said standing position to a position of forward positive flexion with respect to a forward portion of said leg support.

7. The device of claim 6 wherein said forward brace member is provided with a first end portion, which is operatively coupled to a point on said pylon between opposite end portions of said pylon, and a second free end portion that is positioned to releasably engage said leg support to limit movement of said pylon from said standing position to said position of forward positive flexion.

8. The device of claim 7 further comprising a deformably resilient bumper that is positioned to cushion an engagement force between the free end portion of said forward brace member and said leg support.

9. The device of claim 1 wherein said pylon is selectively length adjustable.

10. The device of claim 1 wherein said foot means is comprised of a base having forward and rearward end portions and is pivotably coupled with the distal end portion of said pylon at a point between the forward and rearward end portions of said base so that said pylon may be selectively moved between a standing position, which is generally perpendicular to said base, and a forward positive flexion position with respect to said base.

11. The device of claim 10 further comprising a resilient brace member that is operatively coupled with said base and said pylon in such a manner that said pylon is biased toward said standing position with respect to said base.

12. The device of claim 11 further comprising a bracket that operatively engages said pylon and said base in a manner that limits movement of said pylon from said standing position to a position of rearward positive flexion with respect to said base.

13. An ambulation assistance device for use with an individual's leg, the device comprising:
   a leg support, having upper and lower surfaces; said upper surface being shaped to releasably engage a forward portion of the individual's knee and at least a forward portion of a lower portion of the individual's leg when the lower portion of the individual's leg is positively flexed;
   a generally elongated pylon operatively coupled with and extending downwardly from said leg support;
   foot means adjacent a distal end portion of said pylon for releasably engaging an operating surface and providing positive traction between said pylon and said operating surface; said foot means being comprised of a base having forward and rearward end portions and being pivotably coupled with the distal end portion of said pylon at a point between the forward and rearward end portions of said base so that said pylon may be selectively moved between a standing position, which is generally perpendicular to said base, and a forward positive flexion position with respect to said base;
   a resilient brace member, operatively coupled with said base and said pylon such that said pylon is biased toward said standing position with respect to said base; and
   a bracket that operatively engages said pylon and said base in a manner that limits movement of said pylon from said standing position to a position of rearward positive flexion with respect to said base;
   said bracket being provided with a first end portion, which is operatively coupled to a point on said pylon between opposite end portions of said pylon, and a second free end portion that is positioned to releasably engage said base to limit movement of said pylon from said standing position to said position of rearward positive flexion.

14. The device of claim 13 wherein said pylon is pivotably coupled with said leg support in a manner that permits said pylon to be selectively moved between a standing position, which is generally perpendicular in relationship to said leg support, to a flexion position, which positions said pylon in an acute angular relationship to a rearward portion of said leg support.

15. The device of claim 14 further comprising a resilient rear brace member operatively coupled at one end portion to the rearward portion of said leg support and at an opposite end portion to a point on said pylon that is between opposite end portions of said pylon so that said pylon is based toward said standing position.

16. The device of claim 13 further comprising a forward brace member that operatively engages said pylon and said leg support in a manner that limits movement of said pylon from said standing position to a position of forward positive flexion with respect to a forward portion of said leg support.

17. The device of claim 13 wherein said leg support is angularly shaped to support the individual's leg in a position approximating ninety degrees flexion at the knee and wherein the upper surface of said leg support is shaped to releasably engage a forward portion of an upper portion of the individual's leg.

* * * * *